US011816265B1

United States Patent
Tiku et al.

(10) Patent No.: US 11,816,265 B1
(45) Date of Patent: Nov. 14, 2023

(54) PROVIDING SCENES IN A VIRTUAL ENVIRONMENT BASED ON HEALTH DATA USING EXTENDED REALITY

(71) Applicant: Micron Technology, Inc., Boise, ID (US)

(72) Inventors: Saideep Tiku, Folsom, CA (US); Poorna Kale, Folsom, CA (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 17/823,787

(22) Filed: Aug. 31, 2022

(51) Int. Cl.
*G06F 3/01* (2006.01)

(52) U.S. Cl.
CPC ........ *G06F 3/015* (2013.01); *G06F 2203/011* (2013.01)

(58) Field of Classification Search
CPC ............................ G06F 3/015; G06F 2203/011
USPC ........................................................ 345/156
See application file for complete search history.

(56) References Cited

U.S. PATENT DOCUMENTS

2016/0270656 A1\* 9/2016 Samec .................... A61B 5/361
2021/0129032 A1\* 5/2021 Elenbaas ............... A63F 13/212

\* cited by examiner

*Primary Examiner* — Calvin C Ma
(74) *Attorney, Agent, or Firm* — Harrity & Harrity, LLP

(57) ABSTRACT

In some implementations, an extended reality (XR) device may generate a first event in a virtual environment, wherein the first event is associated with a first difficulty level. The XR device may detect vital information of a user associated with the XR device, wherein the vital information is associated with the first event. The XR device may determine whether the vital information satisfies a threshold. The XR device may transmit, to a server, an indication that indicates whether the vital information satisfies the threshold. The XR device may receive, from the server, virtual environment information, wherein the virtual environment information is based on whether the vital information satisfies the threshold. The XR device may generate, based on the virtual environment information, a second event in the virtual environment, wherein the second event is associated with a second difficulty level.

25 Claims, 10 Drawing Sheets

300

PROVIDING SCENES IN A VIRTUAL ENVIRONMENT BASED ON HEALTH DATA USING EXTENDED REALITY

TECHNICAL FIELD

The present disclosure generally relates to extended reality devices and, for example, providing scenes in a virtual environment based on health data using extended reality.

BACKGROUND

Extended reality (XR) may blend a physical world (or real world) and a virtual world (or digital world) to create a more personalized, immersive visual experience. XR may encompass augmented reality (AR), mixed reality (MR), and virtual reality (VR). AR may provide an interactive experience of a physical-world environment, in which objects that reside in the physical world may be enhanced by computer-generated perceptual information. MR may merge physical and virtual worlds to produce new environments and visualizations, in which physical and digital objects may co-exist and interact in real time. VR may provide a fully virtual world without an intervention of the physical world. XR may be across multiple sensory modalities, including visual, auditory, haptic, somatosensory, and/or olfactory. XR may be useful across a wide variety of applications, such as gaming, healthcare, retail, customer service, and/or manufacturing.

DETAILED DESCRIPTION

Figure 1A:
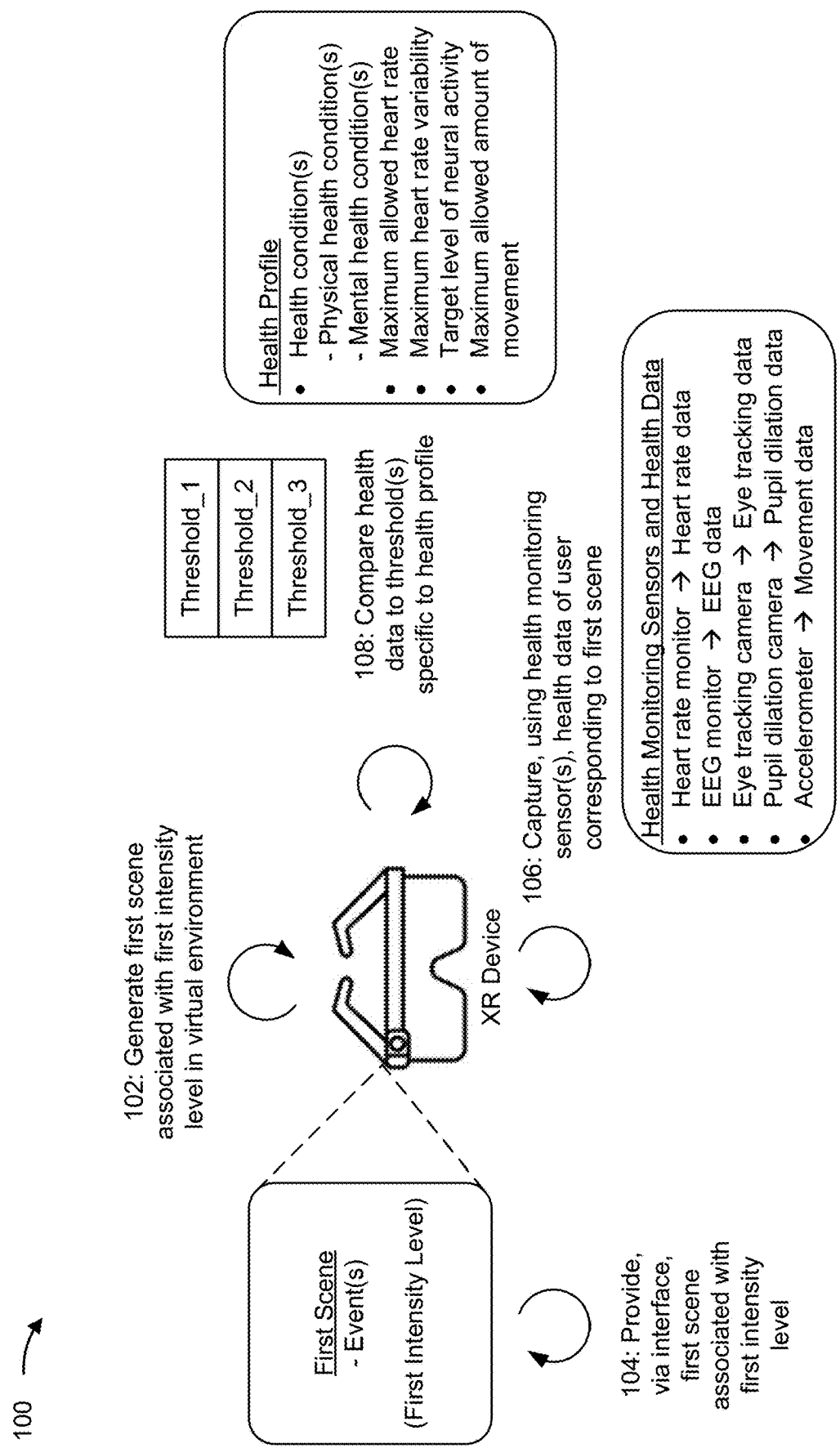
FIGS. 1A-1B are diagrams of an example related to providing scenes in a virtual environment based on health data using extended reality (XR).

A user may interact with a virtual environment using an XR device. The virtual environment may be a three-dimensional virtual environment. The user may wear the XR device (e.g., a head-mounted device). The XR device may run an application (e.g., a gaming application, a fitness application, or a guided meditation application) that provides the virtual environment. The user may perform various virtual actions (e.g., walking, running, or jumping) in the virtual environment. The user may perform real-world physical actions, which may be translated to the virtual actions in the virtual environment. The user may perform a set of virtual actions in the virtual environment in order to move from one level (or scene) in the application to another level in the application. A level in the application may be associated with a certain objective or task, and when the level is satisfied by the user, the level may be passed and a next level may be provided.

One problem with this approach is that the application and/or the XR device may be unaware of the user's general health. The user may be presented with increasingly difficult challenges to perform in the virtual environment, which may involve increasingly difficult real-world physical actions. Such real-world physical actions may result in increased breathing and/or a higher heart rate for the user. Some users may be associated with certain health conditions (e.g., heart disease), or may be at a higher risk for health conditions (e.g., over 65 years of age and obese). The user may be engrossed with the virtual environment, and the user may be unaware when they have reached or exceeded their physical capability. In some cases, the user may experience physical symptoms due to over-exertion, such as dizziness, lightheadedness, chest tightness, and/or fatigue.

Another problem with this approach is that the user may not be completely engaged in the virtual environment. The user may easily complete one level of the application and move onto another level of the application. The application may be unaware that the user is not engaged (or challenged) when performing various virtual actions in the virtual environment. As a result, the user may not have the best experience when interacting with the virtual environment. Further, an unengaging virtual environment may contribute to a waste of computing resources and/or network resources. In other words, the XR device may waste computing and/or network resources by providing the virtual environment.

In some implementations described herein, to solve the problems described above, as well as to provide scenes in a virtual environment that are compatible with user health, a solution is described for providing scenes in a virtual environment based on user health data using XR. An XR device may generate a first scene (or first event or first content) in the virtual environment. The first scene may be associated with a first intensity level. The XR device may capture, using one or more health monitoring sensors of the XR device, health data of a user associated with the XR device. The health data may be associated with the first scene. The health data may indicate an engagement level of the user with respect to the first scene. The XR device may compare the health data to a threshold, where the threshold may be specific to a health profile associated with the user. The XR device may generate a second scene (or second event or second content) in the virtual environment associated with a second intensity level based on whether the health data satisfies the threshold. The XR device may provide, via the interface, the second scene associated with the second intensity level.

In some implementations, the second intensity level may be associated with a higher amount of intensity as compared to an amount of intensity associated with the first intensity level. For example, the second intensity level may be associated with a higher heart rate, a higher heart rate variability, a greater amount of neural activity, and/or a greater amount of pupil dilation, as compared to the first intensity level. Alternatively, the second intensity level may be associated with a lower amount of intensity as compared to the first intensity level. For example, the second intensity level may be associated with a lower heart rate, a lower heart rate variability, a lower amount of neural activity, and/or a lower amount of pupil dilation, as compared to the first intensity level. Alternatively, the first intensity level and the second intensity level may be associated with a similar amount of intensity. In other words, successive scenes may be associated with increasing intensity levels, decreasing intensity levels, or similar intensity levels, which may be based on the health data in relation to the threshold, where the threshold may be specific to the user (e.g., set according to the user's health profile).

In some implementations, users with different health characteristics may be provided with scenes in virtual environments having different intensity levels. In other words, the scenes and/or intensity levels provided to users may be based on their own individual health characteristics, with the idea that different users have different physical capabilities and different health conditions, and as such should be presented with varying intensity levels. For example, a first user that is extremely fit may be provided with a scene in a virtual environment that is more intense than a second user that has heart disease, since the second user may be more susceptible to injury or over-exertion when interacting with the scene in the virtual environment as compared to the first user. As a result, an XR experience may be tailored to the user's health. Users may stay engaged when interacting with the virtual environment. For example, based on a user's health data (e.g., heart rate, breathing variable, neural activity, and/or pupil dilation), the scenes in the virtual environment and/or intensity levels associated with the scenes may be adjusted, such that the user is more likely to be engaged when interacting with the virtual environment.

Figure 1B:
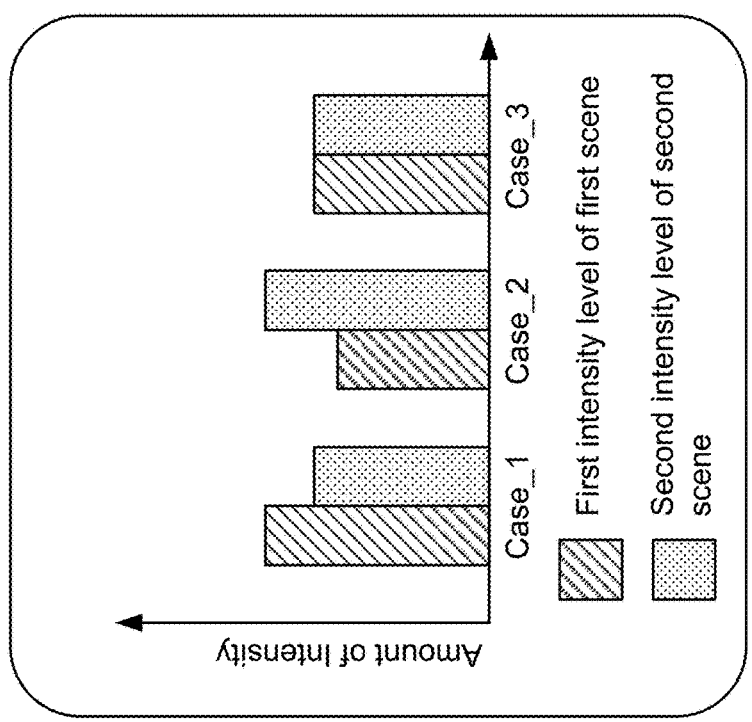

FIGS. 1A-1B are diagrams of an example 100 related to providing scenes in a virtual environment based on health data using XR. As shown in FIGS. 1A-1B, example 100 includes an XR device. This device is described in more detail in connection with FIGS. 5 and 6.

In some implementations, an XR device may be a head-mounted display worn by a user. Alternatively, the XR device may be a mobile device carried by the user. The XR device may provide augmented reality (AR), mixed reality (MR), and/or virtual reality (VR) capabilities. In some implementations, the server may be associated with a cloud computing system or an edge computing system.

In some implementations, the XR device and/or the server may support a deep learning accelerator (DLA). The DLA may be a hardware architecture designed and optimized for increased speed, efficiency, and accuracy when running deep learning algorithms, such as convolutional neural networks (CNNs), recurrent neural networks (RNNs), generative adversarial networks (GANs), and others. The DLA may enable inference tasks to be performed more rapidly and using less energy as compared to general-purpose computers.

In some implementations, the DLA may by supported/used for processing and learning with respect to various tasks. Such tasks, which are further described herein, may include generating scenes in a virtual environment associated with different intensity levels, forming a model of health data associated with performing a virtual task, and/or detecting whether subsequent health data captured by health monitoring sensors corresponds to the model.

As shown in FIG. 1A, and by reference number 102, the XR device may generate a first scene (or first event, first content, or first level) in the virtual environment. The virtual environment may be a three-dimensional environment. The XR device may run or execute an application, which may provide the first scene in the virtual environment. The application may be a gaming application, a fitness application, a guided meditation application, or any other suitable application capable of generating scenes in virtual environments. The first scene may be associated with a given objective or goal. The first scene may be associated with a first intensity level (or first engagement level or first difficulty level). The first scene may include one or more events that are associated with the first intensity level. The first intensity level may be associated with a first set of health data characteristics of the user (e.g., a first heart rate, a first heart rate variability, a first level of neural activity, and/or a first amount of pupil dilation).

As shown by reference number 104, the XR device may provide, via an interface of the XR device, the first scene associated with the first intensity level. The user wearing the XR device may view and interact with the first scene in the virtual environment. The user may interact with the first scene to fulfill the given objective or goal. The user may perform various real-world actions, which may be translated to virtual actions in the first scene in the virtual environment. The virtual actions may include walking, running, jumping, ducking, dodging, etc., which may occur within the first scene in the virtual environment. The first intensity level may be based on the types of virtual actions that need to be performed in order to complete the first scene.

As shown by reference number 106, the XR device may capture, using one or more health monitoring sensors of the XR device, health data of the user (or vital information of the user) associated with the XR device. The health data may be associated with the first scene. In other words, the XR device may capture the health data while the user is interacting with the first scene. The health data may indicate an engagement level of the user with respect to the first scene. In some implementations, the one or more health monitoring sensors may include a heart rate monitor, an electroencephalogram (EEG) monitor, an eye tracking camera, a pupil dilation camera, and/or an accelerometer, and the health data may include heart rate data, EEG data, eye tracking data, pupil dilation data, and/or movement data. The heart rate monitor may collect the heart rate data of the user while the user is interacting with the first scene. The EEG monitor may collect the EEG data of the user while the user is interacting with the first scene. The eye tracking camera may collect the eye tracking data of the user while the user is interacting with the first scene. The pupil dilation camera may collect the pupil dilation data of the user while the user is interacting with the first scene. The accelerometer may collect the movement data of the user while the user is interacting with the first scene.

In some implementations, the health data of the user may be indicative of an emotion associated with the user, where the emotion may correspond to the first scene being provided. The emotion may be one of happiness, sadness, fear, anger, disgust, excitement, or surprise. For example, the health data may include certain values (e.g., heart rate values, heart rate variability values, neural activity levels, and/or neural activity patterns) that are indicative of the user feeling scared when interacting with the first scene in the virtual environment. As another example, the health data may include certain values (e.g., heart rate values, heart rate variability values, neural activity levels, and/or neural activity patterns) that are indicative of the user feeling happy when interacting with the first scene in the virtual environment.

As shown by reference number 108, the XR device may compare the health data to a threshold (or multiple thresholds), where the threshold may be specific to a health profile associated with the user. The health profile may indicate a health condition of the user (e.g., hypertension). The health profile may indicate a maximum allowed heart rate due to the health condition of the user. The health profile may indicate a maximum heart rate variability due to the health condition of the user. The health profile may indicate a target level of neural activity based on the health condition of the user. The health profile may indicate a maximum allowed amount of movement due to the health condition of the user. The health condition may be a physical health condition or a mental health condition. In some cases, the health profile may be stored locally on the XR device for privacy reasons. The threshold may be determined based on the health profile associated with the user. For example, a threshold for a maximum allowed heart rate may be set lower for a user that has hypertension, as compared to a user that does not have hypertension. As another example, a threshold for a maximum heart rate variability may be set lower for the user that has hypertension, as compared to the user that does not have hypertension. Thus, different thresholds may be defined for different users, depending on whether the users have any health conditions and, if so, the types of health conditions.

In some implementations, the threshold may be further specific to a training objective, where the training objective may be based on a type of application that runs on the XR device. For example, the application may be a combat training application or a police training application, in which users are to be trained to handle stressful situations. Depending on the training objective, an ability to handle a certain amount of stress and to stay calm may be important. Therefore, depending on the training objective, the threshold may be adjusted.

As an example, the combat training application may intentionally attempt to apply stress to the user and place the user in a more stressful state. The XR device may monitor the health data of the user to determine how the user is reacting to stressful situations. When the user's stress level starts to increase beyond an acceptable level, the user may be notified and may be provided with a recommendation for lowering their stress level.

As shown in FIG. 1B, and by reference number 110, the XR device may generate a second scene (or second event, second content, or second level) in the virtual environment associated with a second intensity level based on whether the health data satisfies the threshold. The second scene may be associated with a given objective or goal. The second scene may be associated with the second intensity level (or second engagement level or second difficulty level). The second scene may include one or more events that cause the second intensity level. The second intensity level may be associated with a second set of health data characteristics of the user (e.g., a second heart rate, a second heart rate variability, a second level of neural activity, and/or a second amount of pupil dilation).

In some implementations, the second intensity level of the second scene may be associated with a higher amount of intensity as compared to the first intensity level of the first scene, depending on whether the health data satisfies the threshold. For example, the second intensity level may be associated with a higher heart rate, a higher heart rate variability, a greater amount of neural activity, and/or a greater amount of pupil dilation, as compared to the first intensity level. In some implementations, the second intensity level of the second scene may be associated with a lower amount of intensity as compared to the first intensity level of the first scene, depending on whether the health data satisfies the threshold. For example, the second intensity level may be associated with a lower heart rate, a lower heart rate variability, a lower amount of neural activity, and/or a lower amount of pupil dilation, as compared to the first intensity level. In some implementations, the first intensity level of the first scene and the second intensity level of the second scene may be associated with a similar amount of intensity, depending on whether the health data satisfies the threshold. In other words, successive scenes may be associated with increasing intensity levels, decreasing intensity levels, or similar intensity levels, which may be based on the health data in relation to the threshold, where the threshold may be specific to the user (e.g., set according to the user's health profile). In some implementations, a scene that is more intense or that has higher intensity, as compared to another scene, may be associated with a greater amount of stimulation to the user (e.g., more movement, more effort, more blinking lights, louder music, and/or more stress).

As an example, a first user may be physically fit with no health conditions. When interacting with the first scene in the virtual environment, the health data captured for the first user may indicate that the first user's heart rate, heart rate variability, and/or pupil dilation were below a threshold, where the threshold may have previously been defined for the first user based on the first user's health profile. In this case, the first user may be presented with a second scene in the virtual environment that is more intense as compared to the first scene. The first user may be capable of exerting themselves harder, so the first user may be presented with a more intense scene. The more intense scene may cause the first user's heart rate, heart rate variability, and/or pupil dilation to increase, which may cause the first user to be more engaged.

As another example, a second user may be an elderly user having high blood pressure. When interacting with a scene in the virtual environment that is associated with a high intensity, the health data captured for the second user may indicate that the second user's heart rate and/or heart rate variability were above a threshold or were approaching the threshold, where the threshold may have previously been defined for the second user based on the second user's health profile. In this case, the second user may be presented with another scene in the virtual environment that is less intense or equally as intense as compared to the first scene. The second user may not be capable of exerting themselves harder, and/or doing so may pose a health risk, so the second user may be presented with a less intense scene. The less intense scene may cause the second user's heart rate and/or heart rate variability to decrease, which may be preferred given the second user's health condition.

As shown by reference number 110, the XR device may generate, via the interface of the XR device, the second scene associated with the second intensity level. The user wearing the XR device may view and interact with the second scene in the virtual environment. The user may interact with the second scene to fulfill the given objective or goal. The user may perform various real-world actions, which may be translated to virtual actions in the second scene in the virtual environment. The second intensity level may be based on the types of virtual actions that need to be performed in order to complete the second scene.

As an example, in a gaming application, the XR device may provide, via the interface, a first scene in which the user associated with the XR device is to battle a monster that is supposed to be scary. The XR device may capture a heart rate of the user when the user is battling the monster. When the heart rate indicates that the scary monster is not in fact scary for the user, the XR device may provide, via the interface, a second scene in which the user is to battle another monster. The other monster may have different characteristics, which may be expected to provoke an increased heart rate for the user (e.g., a more scared reaction from the user). The determination as to whether the monster is scary may be specific to the user based on the user's health profile, and different determinations may be made for different users based on their respective health profiles.

As another example, in a guided meditation application, the XR device may provide, via the interface, a first scene in which the user associated with the XR device is supposed to follow a breathing technique. The XR device may capture a respiratory rate of the user when the user is following the breathing technique. The XR device may capture other health data, such as a heart rate and neural activity. At the end of the first scene, the XR device may determine whether the respiratory rate of the user satisfies a threshold. In this case, the user may be an expert in guided meditation, so the threshold may be set based on the user's guided meditation expertise. When the respiratory rate of the user during the first scene satisfies the threshold (e.g., the respiratory rate is sufficiently low), the XR device may provide, via the interface, a second scene in which the user is supposed to follow a more advanced version of the breathing technique. The second scene may involve adjusted instructions or guidance as compared to the first scene. When the respiratory rate of the user during the first scene does not satisfy the threshold (e.g., the respiratory rate is too high), the XR device may provide a notification, where the notification may indicate suggestions for lowering the user's breathing rate.

In some implementations, the XR device may provide, via the interface, a notification indicating whether the health data satisfies the threshold. The notification may indicate whether the health data, which may be associated with the first scene, satisfies the threshold. The XR device may provide the notification at the end of the first scene, or at the beginning of the second scene. The notification may indicate to the user whether the second scene is associated with a higher intensity or a lower intensity as compared to the first scene. The notification may include messages to the user to slow down or work harder, depending on whether the health data associated with the first scene satisfies the threshold. As a result, the user may be informed as to whether the second scene will be more difficult or less difficult as compared to the first scene.

In some implementations, the XR device may process (e.g., using the DLA of the XR device) signals from the one or more health monitoring sensors. The XR device may process the signals using a buffer, such as a dynamic capacity ping-pong buffer. The XR device may filter the signals in hardware and/or software. The XR device may perform a machine learning or computer vision based user state detection, which may indicate a behavior of the user. In other words, the XR device may detect a user reactivity based on scenes in the virtual environment. Such information may be inputted to the application running on the XR device. The XR device may use the information when generating a next scene with another intensity level.

In some implementations, the one or more health monitoring sensors may enable an emotional and psychological feedback loop to the application running on the XR device, which may enable the detection of psychological excitement to create a tailored user experience. The XR device may detect the user reactivity to content being fed into the XR device by correlating inertial measurement unit (IMU) and camera movements with health data (e.g., heart rate). The XR device may detect events or episodes for which the user's health data (e.g., heart rate) is responding to the content fed into the XR device. The XR device may detect the content being fed into the XR device, and then adjust an intensity of subsequent content (e.g., content seen and experienced by the user) based on the user's health data.

Figure 1B:
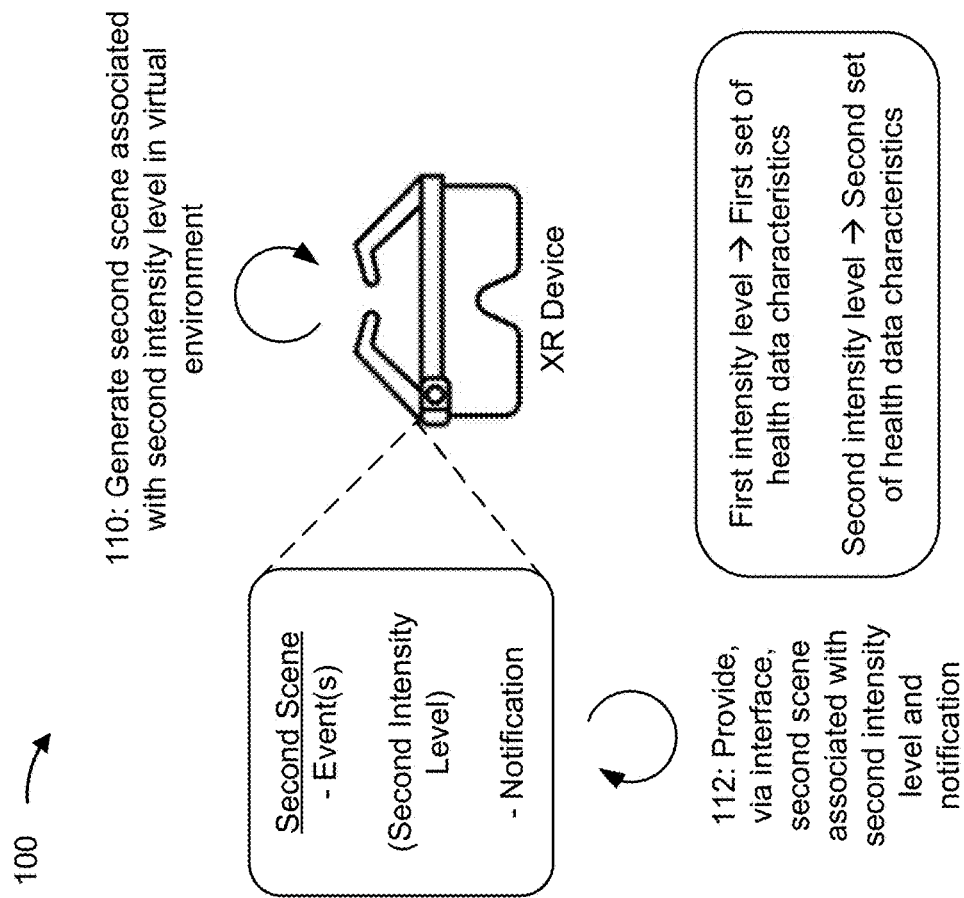

As indicated above, FIG. 1 is provided as an example. Other examples may differ from what is described with regard to FIG. 1.

Figure 2A:
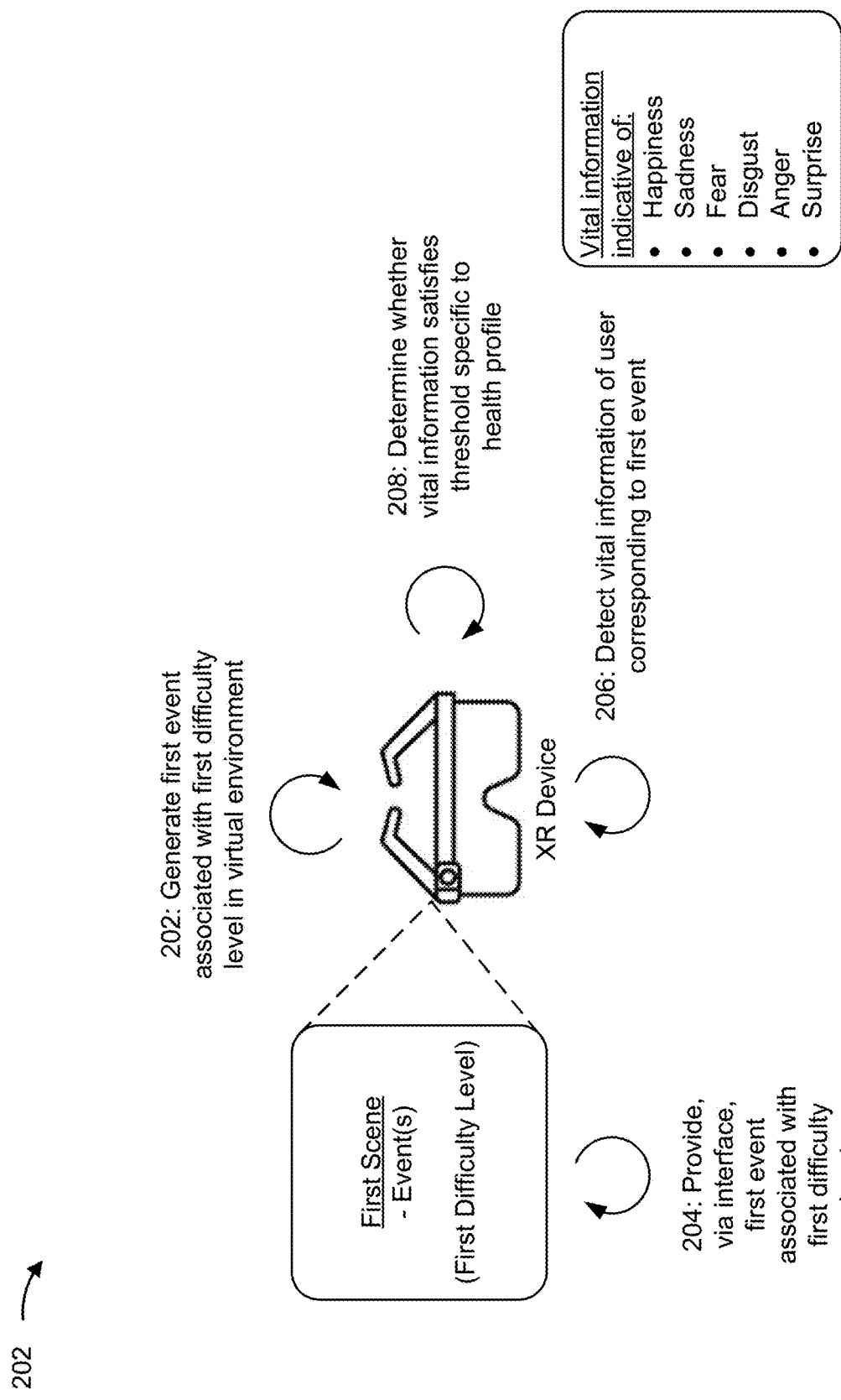
FIGS. 2A-2B are diagrams of an example related to providing events in a virtual environment based on vital information using XR.
Figure 2B:
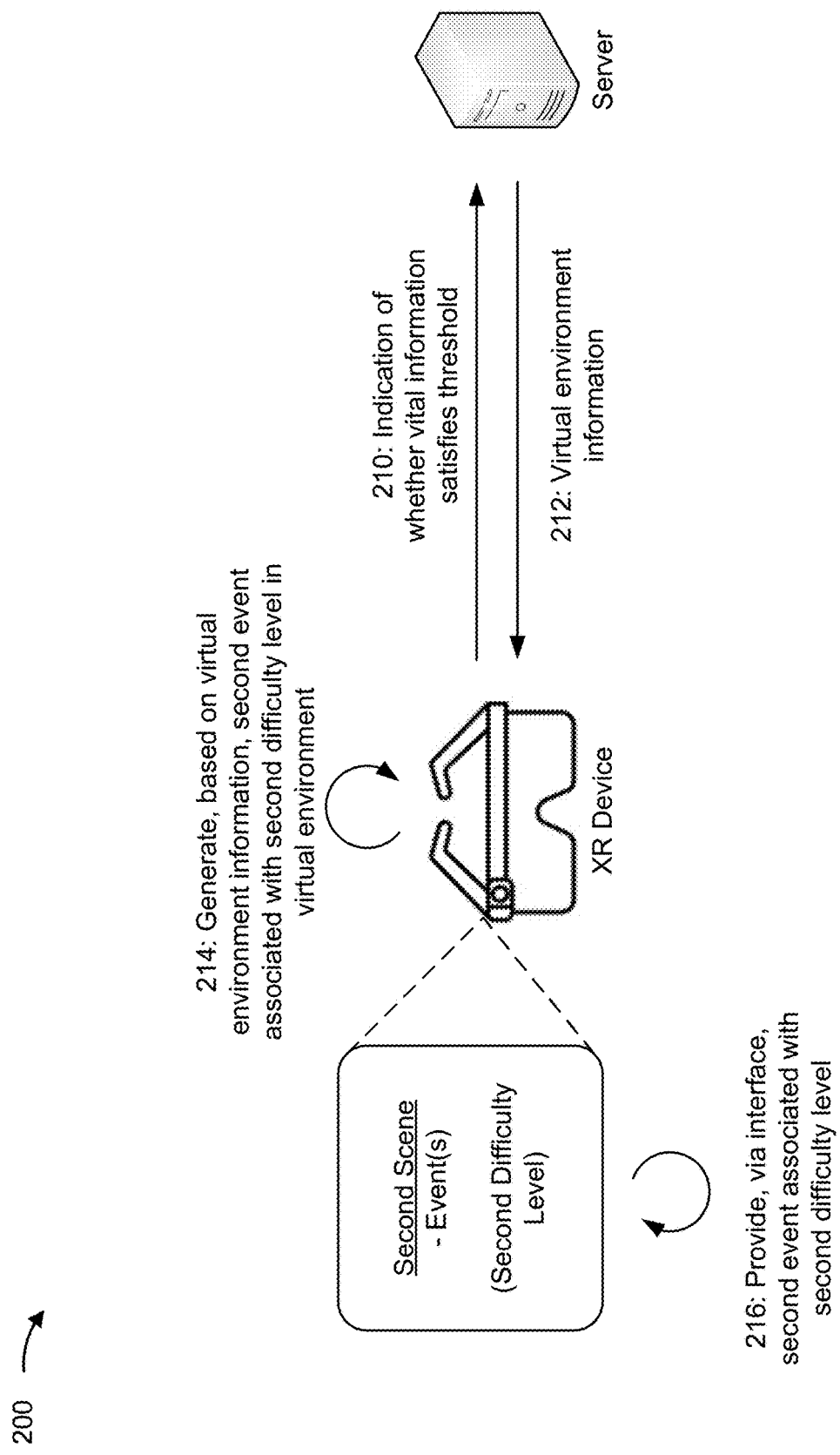

FIGS. 2A-2B are diagrams of an example 200 related to providing events in a virtual environment based on virtual information using XR. As shown in FIGS. 2A-2B, example 200 includes an XR device and a server. These devices are described in more detail in connection with FIGS. 5 and 6.

As shown in FIG. 2A, and by reference number 202, the XR device may generate a first event (or first scene, first content, or first level) in the virtual environment. The virtual environment may be a three-dimensional environment. The XR device may run or execute an application, which may provide the first event in the virtual environment. The application may be a gaming application, a guided meditation application, a fitness application, or any other suitable application capable of generating scenes in virtual environments. The first event may be associated with a given objective or goal. The first event may be associated with a first difficulty level (or first intensity level or first engagement level). The first event may be associated with certain features that cause the first intensity level. The first difficulty level may be associated with a first set of vitals of the user (e.g., a first heart rate, a first heart rate variability, a first level of neural activity, and/or a first amount of pupil dilation).

As shown by reference number 204, the XR device may provide, via an interface of the XR device, the first event associated with the first difficulty level. The user wearing the XR device may view and interact with the first event in the virtual environment. The user may interact with the first event to fulfill the given objective or goal. The user may perform various real-world actions, which may be translated to virtual actions in the first event in the virtual environment. The first difficulty level may be based on the types of virtual actions that need to be performed in order to complete the first event.

As shown by reference number 206, the XR device may capture, using one or more health monitoring sensors of the XR device, vital information of the user (or health data of the user) associated with the XR device. The vital information may be associated with the first event. In other words, the XR device may capture the vital information while the user is interacting with the first event. The vital information may be indicative of an emotion (e.g., happiness, sadness, fear, anger, disgust, excitement, or surprise) associated with the user. The user may exhibit the emotion when interacting with the first event.

As shown by reference number 208, the XR device may determine whether the vital information satisfies a threshold (or multiple thresholds), where the threshold may be specific to a health profile associated with the user. The XR device may compare the vital information to the threshold. The health profile may indicate a health condition of the user, a maximum allowed heart rate due to the health condition of the user, a maximum heart rate variability due to the health condition of the user, a target level of neural activity based on the health condition of the user, a maximum allowed amount of movement due to the health condition of the user, and/or other health metrics. The health condition may be a physical health condition or a mental health condition.

As shown in FIG. 2B, and by reference number 210, the XR device may transmit, to the server, an indication that indicates whether the vital information satisfies the threshold. For example, the XR device may indicate whether a heart rate of the user during the first event exceeds a threshold that is specific to the user. As another example, the XR device may indicate whether a respiration rate of the user during the first event exceeds a threshold that is specific to the user. Thresholds for the heart rate and the respiration rate may be different for the user. In other words, one threshold may be defined for the heart rate for the user, and another threshold may be defined for the respiration rate for the user.

As shown by reference number 212, the server may transmit virtual environment information to the XR device, which may be based on the indication received from the XR device. In other words, the virtual environment information may be based on whether the vital information satisfies the threshold. The server may receive the indication from the XR device. The server may generate the virtual environment information based on the indication. The virtual environment information may include event information (or scene information), which may be used by the XR device to generate a second event (or second scene, second content, or second level). The virtual environment information used to generate the second event may be different from virtual environment information used to generate the first event.

As shown by reference number 214, the XR device may generate, based on the virtual environment information, the second event (or second scene, second content, or second level) in the virtual environment. The second event may be associated with a second difficulty level (or second intensity level or second engagement level), which may be based on the virtual environment information, where the virtual environment information may be based on whether the vital information satisfies the threshold. The second event may be associated with a given objective or goal. The second event may be associated with certain features that cause the first intensity level. The second difficulty level may be associated with a second set of vitals of the user (e.g., a second heart rate, a second heart rate variability, a second level of neural activity, and/or a second amount of pupil dilation). The second set of vitals may be different from the first set of vitals.

In some implementations, the server may determine the virtual environment information based on information collected from a plurality of XR devices. The information may indicate whether vital information corresponding to a plurality of users satisfies a generic threshold for events with certain difficulty levels. In other words, each XR device, of the plurality of XR devices, may transmit to the server information regarding whether vital information of a user collected during an event satisfies the generic threshold. The generic threshold may be different from user-specific thresholds. The server may be able to determine which events cause users' vital information to satisfy thresholds and which events cause users' vital information to not satisfy thresholds. The server may determine which events are likely or not likely to cause users to feel scared, excited, sad, happy, angry, etc. The server may use this information when determining the virtual environment information, which may be transmitted to the XR device. As a result, the XR device may generate the second event having the second difficulty level using the virtual environment information that is based on information collected from the plurality of XR devices.

As shown by reference number 216, the XR device may provide, via the interface of the XR device, the second event associated with the second difficulty level. The user wearing the XR device may view and interact with the second event in the virtual environment. The user may interact with the second event to fulfill the given objective or goal. The user may perform various real-world actions, which may be translated to virtual actions in the second event in the virtual environment. The second difficulty level may be based on the types of virtual actions that need to be performed in order to complete the second event. In some implementations, the XR device may provide, via the interface, a notification that indicates whether the second event is less intense or more intense than the first event based on the vital information.

As indicated above, FIG. 2 is provided as an example. Other examples may differ from what is described with regard to FIG. 2.

Figure 3:
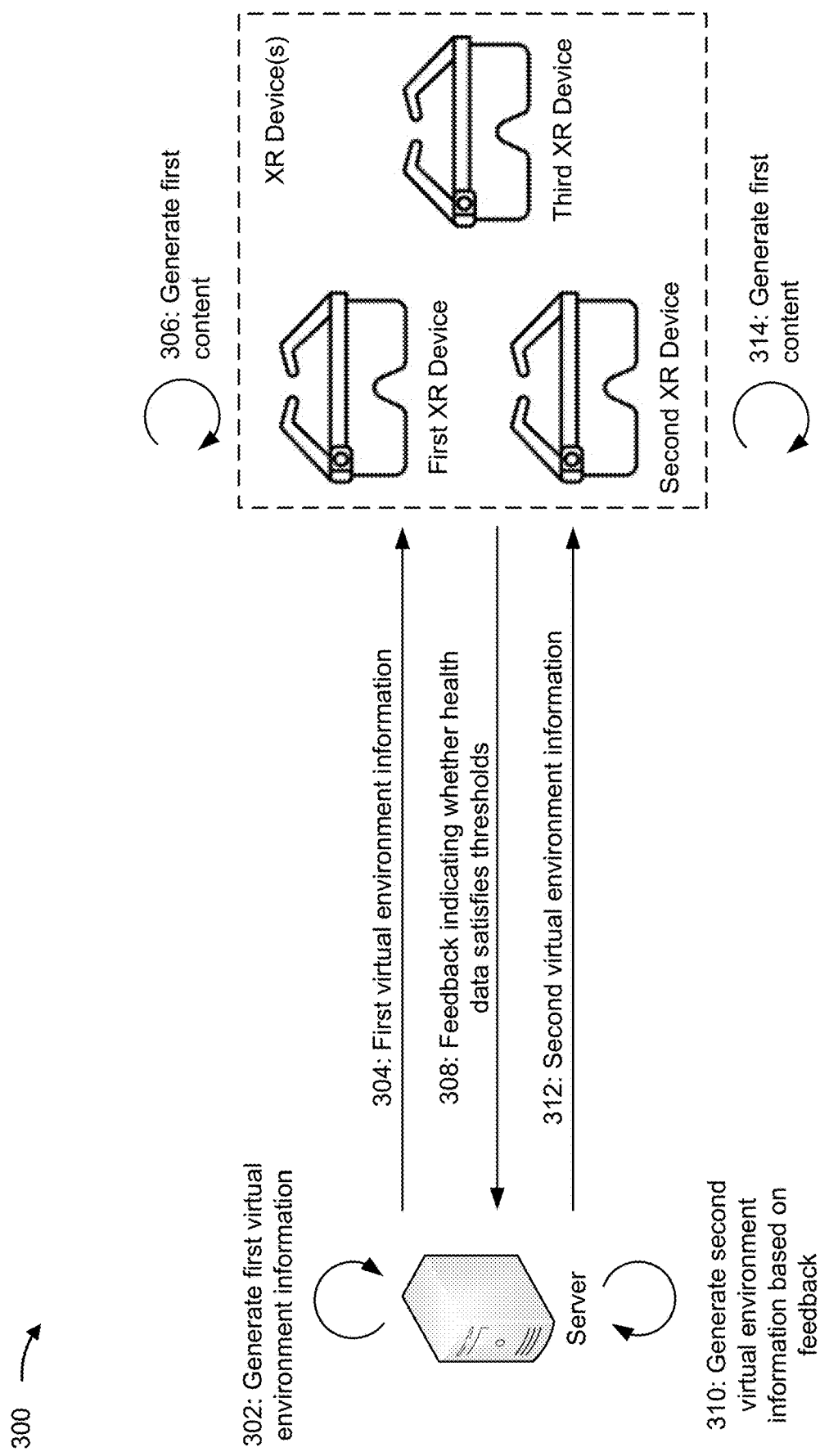
FIG. 3 is a diagram illustrating an example related to generating virtual environment information based on feedback received from XR devices.

FIG. 3 is a diagram of an example 300 related to generating virtual environment information based on feedback received from XR devices. As shown in FIG. 3, example 300 includes a plurality of XR devices and a server. These devices are described in more detail in connection with FIGS. 5 and 6.

As shown by reference number 302, the server may generate first virtual environment information. The first virtual environment information may be associated with a first content (or first scene or first event), where the first content may be associated with a first intensity level. The first content may be associated with a gaming application, a fitness application, or a guided meditation application. The first content may be associated with a three-dimensional environment.

As shown by reference number 304, the server may transmit, to the plurality of XR devices, the first virtual environment information. For example, the server may transmit the first virtual environment information to a first XR device, a second XR device, and a third XR device of the plurality of XR devices.

As shown by reference number 306, the plurality of XR devices may each generate the first content based on the first virtual environment information. The plurality of XR devices may each provide, via respective interfaces, the first content having the first intensity level.

As shown by reference number 308, the plurality of XR devices may each transmit, to the server, feedback indicating whether health data associated with the first content satisfies one or more thresholds, where the health data may be associated with a plurality of users associated with the plurality of XR devices, respectively. In other words, each XR device may indicate, to the server, whether health data of a user of the XR device satisfies a threshold when the user is interacting with the first content. The server may receive such information from each of the plurality of XR devices. The server may aggregate this information, from which the server may determine which content produces user health data that satisfies a threshold and which content produces user health data that does not satisfy the threshold.

As shown by reference number 310, the server may generate, based on the feedback, second virtual environment information. The second virtual environment information may be associated with a second content (or second scene or second event), where the second content may be associated with a second intensity level. In other words, depending on the feedback received from the plurality of users, the server may adjust the first virtual environment information to obtain the second virtual environment information.

As shown by reference number 312, the server may transmit to the plurality of XR devices, the second virtual environment information. For example, the server may transmit the second virtual environment information to the first XR device, the second XR device, and the third XR device of the plurality of XR devices.

As shown by reference number 314, the plurality of XR devices may each generate the second content based on the second virtual environment information. The plurality of XR devices may each provide, via respective interfaces, the second content having the second intensity level.

In some implementations, the server may assist the plurality of XR devices in generating the content, as opposed to the XR devices generating the content independent of the server. The server may collect the information from the plurality of XR devices, and the server may assist other XR devices based on this information. In other words, virtual environment information used by one XR device to generate content may be based on feedback received from other XR devices. As a result, the server may provide virtual environment information that results in better content generated by the XR devices.

As an example, the server may generate virtual environment information associated with an event that is supposed to be scary. For example, the event may be intended to increase the heart rate and breathing rate of a user that is exposed to the event. The server may transmit the virtual environment information to the plurality of XR devices. The server may receive, from the plurality of XR devices, feedback regarding user health data (e.g., heart rate data and breathing rate data of users) in relation to thresholds, which may indicate whether the event is actually scary to users associated with the XR devices. Based on the feedback, the server may generate subsequent virtual environment information associated with a scarier event or a less scary event. When a majority of users find the initial event to not be scary, the server may adjust the virtual environment information accordingly to create additional scariness in the latter event. The server may receive the feedback and dynamically adjust the subsequent virtual environment information associated with a next scene accordingly.

As indicated above, FIG. 3 is provided as an example. Other examples may differ from what is described with regard to FIG. 3.

Figure 4:
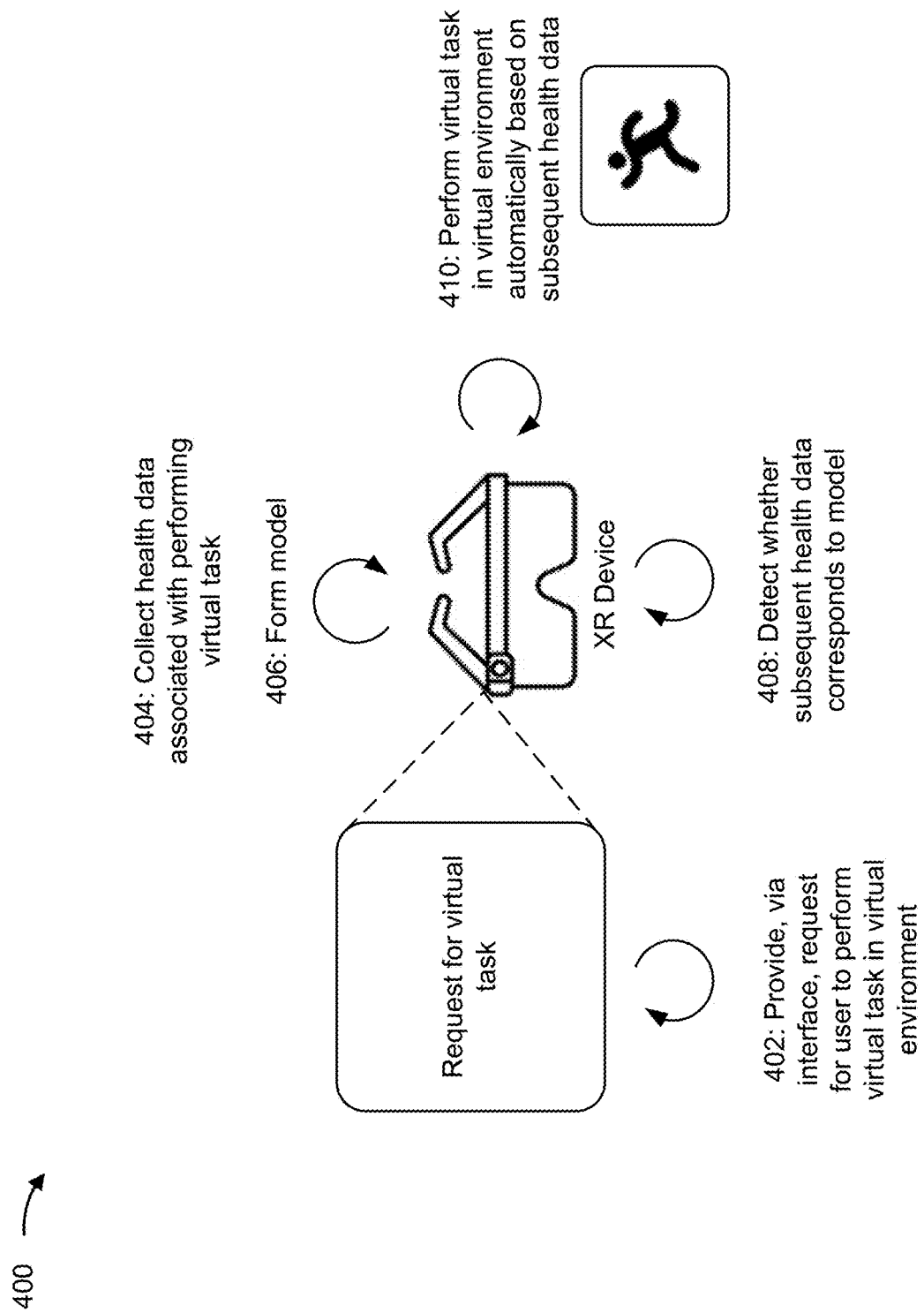
FIG. 4 is a diagram illustrating an example related to performing virtual tasks in a virtual environment.

FIG. 4 is a diagram of an example 400 related to performing virtual tasks in a virtual environment. As shown in FIG. 4, example 400 includes an XR device. This device is described in more detail in connection with FIGS. 5 and 6.

As shown by reference number 402, the XR device may provide, via an interface of the XR device, a request for a user associated with the XR device to perform a virtual task in the virtual environment. The virtual task may be any sort of task, such as a short burst of running, opening a door in the virtual environment, or turning on a light in the virtual environment.

As shown by reference number 404, the XR device may collect, based on the request and using the one or more health monitoring sensors, health data associated with performing the virtual task. For example, the XR device may include an EEG sensor that collects EEG data of the user when the user is performing the virtual task in the virtual environment. The EEG data may be neural activity that is expressed in electrical signals. In some implementations, the XR device may prompt the user to perform the virtual task multiple times, and each time, the XR device may collect EEG data associated with the user performing the virtual task.

As shown by reference number 406, the XR device may form a model of the health data associated with performing the virtual task. The model may indicate typical health data of the user when the user performs the virtual task. For example, the XR device may form the model based on the electrical signals associated with the neural activity.

As shown by reference number 408, the XR device may detect whether subsequent health data captured by the one or more health monitoring sensors corresponds to the model. For example, the XR device may determine whether subsequent EEG data collected by the EEG sensor corresponds to the model. As shown by reference number 410, the XR device may perform the virtual task in the virtual environment automatically based on the subsequent health data corresponding to the model. The XR device may determine that the subsequent health data is similar to the model, and as a result, the XR device may initiate the virtual task associated with the model to be automatically performed in the virtual environment. In some cases, the XR device may provide, via the interface, a prompt to request the user to verify that the virtual task is to be performed in the virtual environment. After providing the prompt a certain number of times, and after receiving a same response from the user each time, the XR device may no longer provide the prompt.

As indicated above, FIG. 4 is provided as an example. Other examples may differ from what is described with regard to FIG. 4.

Figure 5:
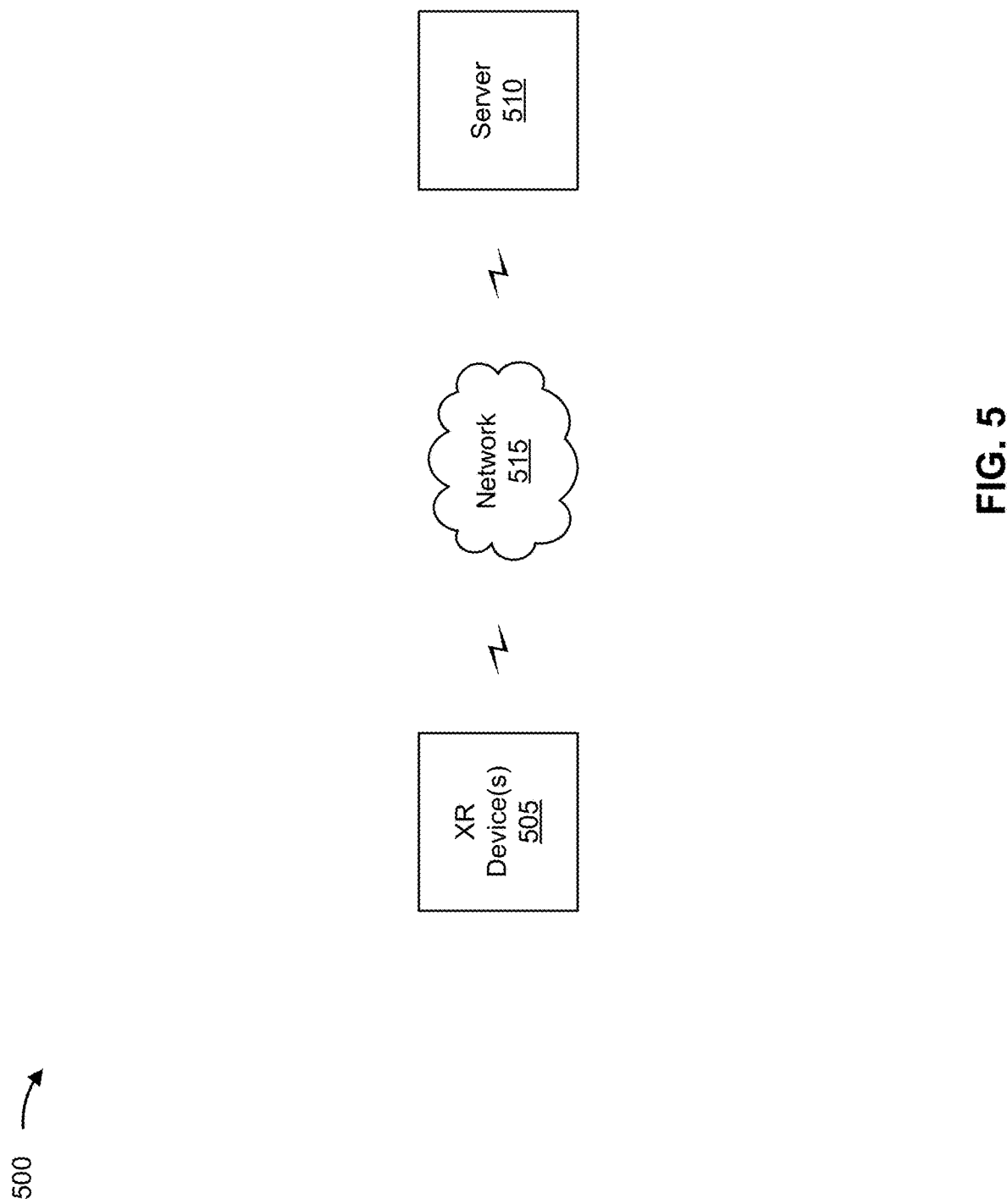
FIG. 5 is a diagram illustrating an example environment in which systems and/or methods described herein may be implemented.

FIG. 5 is a diagram of an example environment 500 in which systems and/or methods described herein may be implemented. As shown in FIG. 5, environment 300 may include one or more XR devices 505, a server 510, and a network 515. Devices of environment 500 may interconnect via wired connections, wireless connections, or a combination of wired and wireless connections.

An XR device 505 may be capable of receiving, generating, storing, processing, providing, and/or routing information associated with providing scenes in a virtual environment based on health data using XR, as described elsewhere herein. The XR device 505 may be a head-mounted device (or headset) or a mobile device. The XR device 505 may provide XR capabilities, which may include AR, MR, and/or VR. The XR device 505 may include various types of hardware, such as processors, sensors, cameras, input devices, and/or displays. The sensors may include accelerometers, gyroscopes, magnetometers, and/or eye-tracking sensors. The XR device 505 may include an optical head-mounted display, which may allow information to be superimposed onto a field of view.

The server 510 includes one or more devices capable of receiving, generating, storing, processing, providing, and/or routing information associated with providing scenes in a virtual environment based on health data using XR, as described elsewhere herein. The server 510 may include a communication device and/or a computing device. For example, the server 510 may be an application server, a client server, a web server, a database server, a host server, a proxy server, a virtual server (e.g., executing on computing hardware), or a server in a cloud computing system. In some implementations, the server 510 includes computing hardware used in a cloud computing environment. In some implementations, the server 510 may be part of a cloud computing system or an edge computing system.

The network 515 includes one or more wired and/or wireless networks. For example, the network 515 may include a cellular network, a public land mobile network, a local area network, a wide area network, a metropolitan area network, a telephone network, a private network, the Internet, and/or a combination of these or other types of networks. The network 515 enables communication among the devices of environment 500.

The number and arrangement of devices and networks shown in FIG. 5 are provided as an example. In practice, there may be additional devices and/or networks, fewer devices and/or networks, different devices and/or networks, or differently arranged devices and/or networks than those shown in FIG. 5. Furthermore, two or more devices shown in FIG. 5 may be implemented within a single device, or a single device shown in FIG. 5 may be implemented as multiple, distributed devices. Additionally, or alternatively, a set of devices (e.g., one or more devices) of environment 500 may perform one or more functions described as being performed by another set of devices of environment 500.

Figure 6:
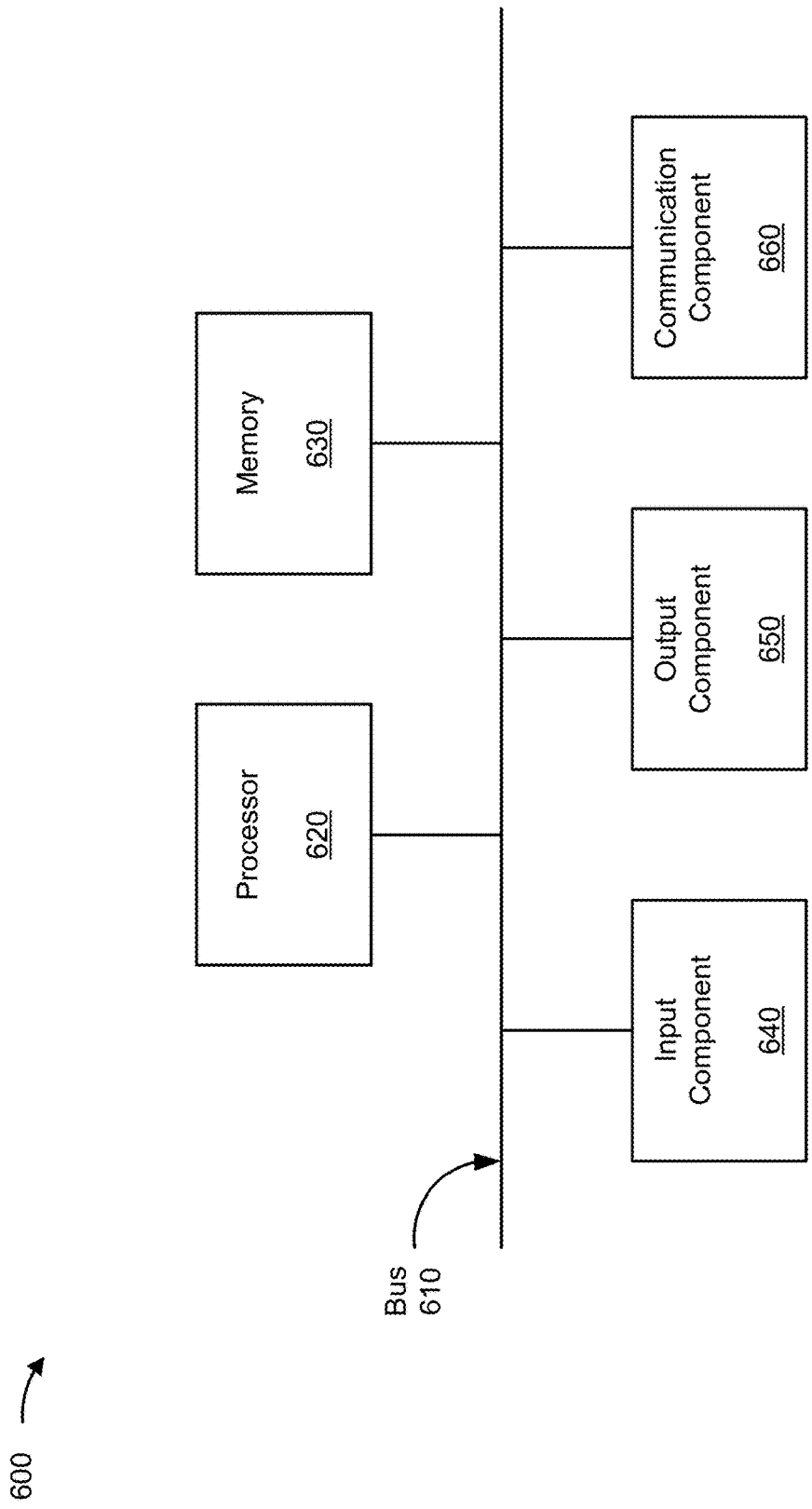
FIG. 6 is a diagram of example components of one or more devices of FIG. 5.

FIG. 6 is a diagram of example components of a device 600 associated with providing scenes in a virtual environment based on health data using XR. Device 600 may correspond to XR device 505 and/or server 510. In some implementations, XR device 505 and/or server 510 may include one or more devices 600 and/or one or more components of device 600. As shown in FIG. 6, device 600 may include a bus 610, a processor 620, a memory 630, an input component 640, an output component 650, and a communication component 660.

Bus 610 may include one or more components that enable wired and/or wireless communication among the components of device 600. Bus 610 may couple together two or more components of FIG. 6, such as via operative coupling, communicative coupling, electronic coupling, and/or electric coupling. Processor 620 may include a central processing unit, a graphics processing unit, a microprocessor, a controller, a microcontroller, a digital signal processor, a field-programmable gate array, an application-specific integrated circuit, and/or another type of processing component. Processor 620 is implemented in hardware, firmware, or a combination of hardware and software. In some implementations, processor 620 may include one or more processors capable of being programmed to perform one or more operations or processes described elsewhere herein.

Memory 630 may include volatile and/or nonvolatile memory. For example, memory 630 may include random access memory (RAM), read only memory (ROM), a hard disk drive, and/or another type of memory (e.g., a flash memory, a magnetic memory, and/or an optical memory). Memory 630 may include internal memory (e.g., RAM, ROM, or a hard disk drive) and/or removable memory (e.g., removable via a universal serial bus connection). Memory 630 may be a non-transitory computer-readable medium. Memory 630 stores information, instructions, and/or software (e.g., one or more software applications) related to the operation of device 600. In some implementations, memory 630 may include one or more memories that are coupled to one or more processors (e.g., processor 620), such as via bus 610.

Input component 640 enables device 600 to receive input, such as user input and/or sensed input. For example, input component 640 may include a touch screen, a keyboard, a keypad, a mouse, a button, a microphone, a switch, a sensor, a global positioning system sensor, an accelerometer, a gyroscope, and/or an actuator. Output component 650 enables device 600 to provide output, such as via a display, a speaker, and/or a light-emitting diode. Communication component 660 enables device 600 to communicate with other devices via a wired connection and/or a wireless connection. For example, communication component 660 may include a receiver, a transmitter, a transceiver, a modem, a network interface card, and/or an antenna.

Device 600 may perform one or more operations or processes described herein. For example, a non-transitory computer-readable medium (e.g., memory 630) may store a set of instructions (e.g., one or more instructions or code) for execution by processor 620. Processor 620 may execute the set of instructions to perform one or more operations or processes described herein. In some implementations, execution of the set of instructions, by one or more processors 620, causes the one or more processors 620 and/or the device 600 to perform one or more operations or processes described herein. In some implementations, hardwired circuitry is used instead of or in combination with the instructions to perform one or more operations or processes described herein. Additionally, or alternatively, processor 620 may be configured to perform one or more operations or processes described herein. Thus, implementations described herein are not limited to any specific combination of hardware circuitry and software.

The number and arrangement of components shown in FIG. 6 are provided as an example. Device 600 may include additional components, fewer components, different components, or differently arranged components than those shown in FIG. 6. Additionally, or alternatively, a set of components (e.g., one or more components) of device 600 may perform one or more functions described as being performed by another set of components of device 600.

Figure 7:
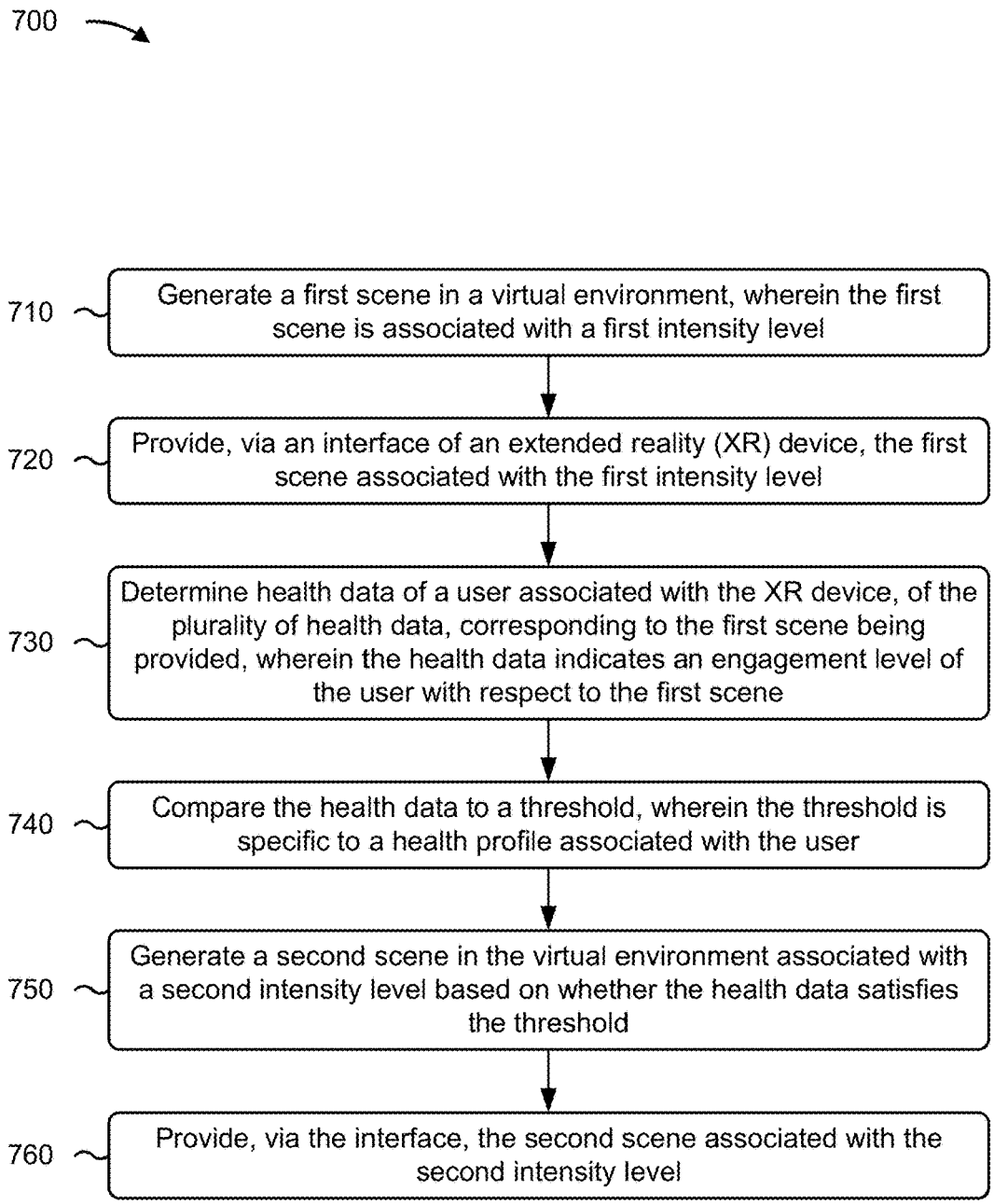
FIG. 7 is a flowchart of an example process relating to providing scenes in a virtual environment based on health data using XR.

FIG. 7 is a flowchart of an example method 700 associated with providing scenes in a virtual environment based on health data using XR. In some implementations, an XR device (e.g., XR device 505) may perform or may be configured to perform one or more process blocks of FIG. 7. In some implementations, another device or a group of devices separate from or including the XR device (e.g., server 510) may perform or may be configured to perform one or more process blocks of FIG. 7. Additionally, or alternatively, one or more components of the XR device (e.g., processor 620, memory 630, input component 640, output component 650, and/or communication component 660) may perform or may be configured to perform one or more process blocks of FIG. 7.

As shown in FIG. 7, the method 700 may include generating a first scene in a virtual environment, wherein the first scene is associated with a first intensity level (block 710). As further shown in FIG. 7, the method 700 may include providing, via an interface of an XR device, the first scene associated with the first intensity level (block 720). As further shown in FIG. 7, the method 700 may include capturing, using one or more health monitoring sensors of the XR device, health data of a user associated with the XR device, wherein the health data is associated with the first scene, and wherein the health data indicates an engagement level of the user with respect to the first scene (block 730). As further shown in FIG. 7, the method 700 may include comparing the health data to a threshold, wherein the threshold is specific to a health profile associated with the user (block 740). As further shown in FIG. 7, the method 700 may include generating a second scene in the virtual environment associated with a second intensity level based on whether the health data satisfies the threshold (block 750). As further shown in FIG. 7, the method 700 may include providing, via the interface, the second scene associated with the second intensity level (block 760).

Although FIG. 7 shows example blocks of a method 700, in some implementations, the method 700 may include additional blocks, fewer blocks, different blocks, or differently arranged blocks than those depicted in FIG. 7. Additionally, or alternatively, two or more of the blocks of the method 700 may be performed in parallel. The method 700 is an example of one method that may be performed by one or more devices described herein. These one or more devices may perform or may be configured to perform one or more other methods based on operations described herein, such as the operations described in connection with FIGS. 1A-1B, 2A-2B, and 3-4.

Figure 8:
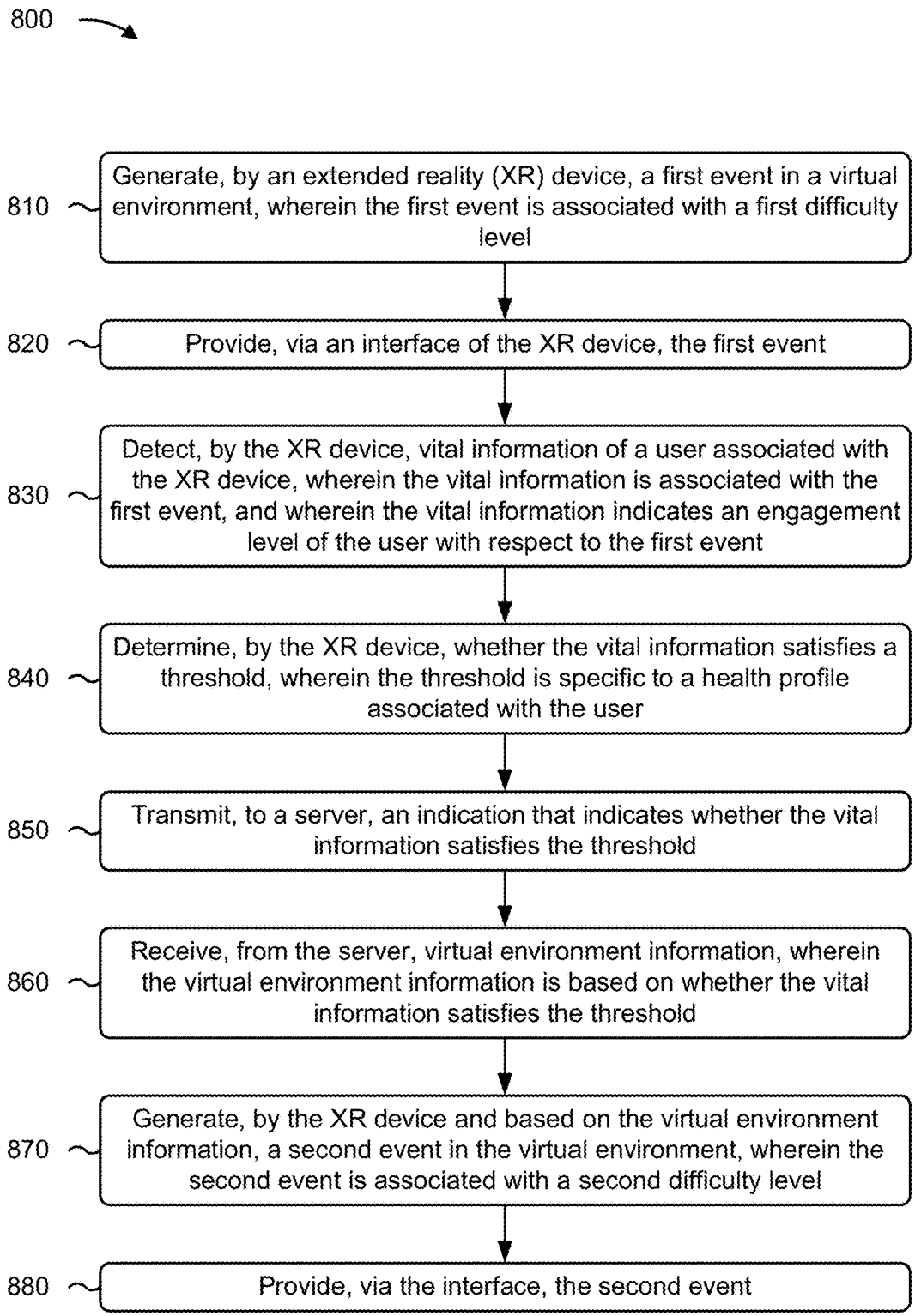
FIG. 8 is a flowchart of an example process relating to providing events in a virtual environment based on virtual information using XR.

FIG. 8 is a flowchart of an example method 800 associated with providing scenes in a virtual environment based on health data using XR. In some implementations, an XR device (e.g., XR device 505) may perform or may be configured to perform one or more process blocks of FIG. 8. In some implementations, another device or a group of devices separate from or including the XR device (e.g., server 510) may perform or may be configured to perform one or more process blocks of FIG. 8. Additionally, or alternatively, one or more components of the XR device (e.g., processor 620, memory 630, input component 640, output component 650, and/or communication component 660) may perform or may be configured to perform one or more process blocks of FIG. 8.

As shown in FIG. 8, the method 800 may include generating, by an XR device, a first event in a virtual environment, wherein the first event is associated with a first difficulty level (block 810). As further shown in FIG. 8, the method 800 may include providing, via an interface of the XR device, the first event (block 820). As further shown in FIG. 8, the method 800 may include detecting, by the XR device, vital information of a user associated with the XR device, wherein the vital information is associated with the first event, and wherein the vital information indicates an engagement level of the user with respect to the first event (block 830). As further shown in FIG. 8, the method 800 may include determining, by the XR device, whether the vital information satisfies a threshold, wherein the threshold is specific to a health profile associated with the user (block 840). As further shown in FIG. 8, the method 800 may include transmitting, to a server, an indication that indicates whether the vital information satisfies the threshold (block 850). As further shown in FIG. 8, the method 800 may include receiving, from the server, virtual environment information, wherein the virtual environment information is based on whether the vital information satisfies the threshold (block 860). As further shown in FIG. 8, the method 800 may include generating, by the XR device and based on the virtual environment information, a second event in the virtual environment, wherein the second event is associated with a second difficulty level (block 870). As further shown in FIG. 8, the method 800 may include providing, via the interface, the second event (block 880).

Although FIG. 8 shows example blocks of a method 800, in some implementations, the method 800 may include additional blocks, fewer blocks, different blocks, or differently arranged blocks than those depicted in FIG. 8. Additionally, or alternatively, two or more of the blocks of the method 800 may be performed in parallel. The method 800 is an example of one method that may be performed by one or more devices described herein. These one or more devices may perform or may be configured to perform one or more other methods based on operations described herein, such as the operations described in connection with FIGS. 1A-1B, 2A-2B, and 3-4.

In some implementations, an extended reality (XR) device includes one or more components configured to: generate a first scene in a virtual environment, wherein the first scene is associated with a first intensity level; provide, via an interface of the XR device, the first scene associated with the first intensity level; capture, using one or more health monitoring sensors of the XR device, health data of a user associated with the XR device, wherein the health data is associated with the first scene, and wherein the health data indicates an engagement level of the user with respect to the first scene; compare the health data to a threshold, wherein the threshold is specific to a health profile associated with the user; generate a second scene in the virtual environment associated with a second intensity level based on whether the health data satisfies the threshold; and provide, via the interface, the second scene associated with the second intensity level.

In some implementations, a method includes generating, by an extended reality (XR) device, a first event in a virtual environment, wherein the first event is associated with a first difficulty level; providing, via an interface of the XR device, the first event; detecting, by the XR device, vital information of a user associated with the XR device, wherein the vital information is associated with the first event, and wherein the vital information indicates an engagement level of the user with respect to the first event; determining, by the XR device, whether the vital information satisfies a threshold, wherein the threshold is specific to a health profile associated with the user; transmitting, to a server, an indication that indicates whether the vital information satisfies the threshold; receiving, from the server, virtual environment information, wherein the virtual environment information is based on whether the vital information satisfies the threshold; generating, by the XR device and based on the virtual environment information, a second event in the virtual environment, wherein the second event is associated with a second difficulty level; and providing, via the interface, the second event.

In some implementations, a system includes a plurality of extended reality (XR) devices; and a server comprising one or more components configured to: generate first virtual environment information for generating first content associated with first intensity levels; transmit, to the plurality of XR devices, the first virtual environment information; receive, from the plurality of XR devices, feedback indicating whether health data associated with the first content satisfies one or more thresholds, wherein the health data is associated with a plurality of users associated with the plurality of XR devices, respectively; generate, based on the feedback, second virtual environment information for generating second content associated with second intensity levels that are different from the first intensity levels; and transmit, to the plurality of XR devices, the second virtual environment information.

The foregoing disclosure provides illustration and description but is not intended to be exhaustive or to limit the implementations to the precise forms disclosed. Modifications and variations may be made in light of the above disclosure or may be acquired from practice of the implementations described herein.

The orientations of the various elements in the figures are shown as examples, and the illustrated examples may be rotated relative to the depicted orientations. The descriptions provided herein, and the claims that follow, pertain to any structures that have the described relationships between various features, regardless of whether the structures are in the particular orientation of the drawings, or are rotated relative to such orientation. Similarly, spatially relative terms, such as "below," "beneath," "lower," "above," "upper," "middle," "left," and "right," are used herein for ease of description to describe one element's relationship to one or more other elements as illustrated in the figures. The spatially relative terms are intended to encompass different orientations of the element, structure, and/or assembly in use or operation in addition to the orientations depicted in the figures. A structure and/or assembly may be otherwise oriented (rotated 90 degrees or at other orientations), and the spatially relative descriptors used herein may be interpreted accordingly. Furthermore, the cross-sectional views in the figures only show features within the planes of the cross-sections, and do not show materials behind the planes of the cross-sections, unless indicated otherwise, in order to simplify the drawings.

As used herein, the terms "substantially" and "approximately" mean "within reasonable tolerances of manufacturing and measurement." As used herein, "satisfying a threshold" may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of implementations described herein. Many of these features may be combined in ways not specifically recited in the claims and/or disclosed in the specification. For example, the disclosure includes each dependent claim in a claim set in combination with every other individual claim in that claim set and every combination of multiple claims in that claim set. As used herein, a phrase referring to "at least one of" a list of items refers to any combination of those items, including single members. As an example, "at least one of: a, b, or c" is intended to cover a, b, c, a+b, a+c, b+c, and a+b+c, as well as any combination with multiples of the same element (e.g., a+a, a+a+a, a+a+b, a+a+c, a+b+b, a+c+c, b+b, b+b+b, b+b+c, c+c, and c+c+c, or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Where only one item is intended, the phrase "only one," "single," or similar language is used. Also, as used herein, the terms "has," "have," "having," or the like are intended to be open-ended terms that do not limit an element that they modify (e.g., an element "having" A may also have B). Further, the phrase "based on" is intended to mean "based, at least in part, on" unless explicitly stated otherwise. As used herein, the term "multiple" can be replaced with "a plurality of" and vice versa. Also, as used herein, the term "or" is intended to be inclusive when used in a series and may be used interchangeably with "and/or," unless explicitly stated otherwise (e.g., if used in combination with "either" or "only one of").

What is claimed is:

1. An extended reality (XR) device, comprising:
one or more components configured to:
generate a first scene in a virtual environment, wherein the first scene is associated with a first intensity level;
provide, via an interface of the XR device, the first scene associated with the first intensity level;
collect, using one or more health monitoring sensors, first health data from a user of the XR device while the user performs a virtual task multiple times in the virtual environment, the first health data being indicative of neural activity that is expressed in electrical signals;
form a model of the first health data based on the electrical signals associated with the neural activity;
capture, using one or more health monitoring sensors, second health data of the user, wherein the second health data is associated with the first scene, and wherein the second health data indicates an engagement level of the user with respect to the first scene;
compare the second health data to a threshold, wherein the threshold is specific to a health profile associated with the user;
determine whether the second health data corresponds to the model;
generate a second scene in the virtual environment associated with a second intensity level based on whether the second health data satisfies the threshold and based on whether the second health data corresponds to the model; and
provide, via the interface, the second scene associated with the second intensity level.

2. The XR device of claim 1, wherein the second intensity level of the second scene is associated with a higher amount of intensity as compared to the first intensity level of the first scene.

3. The XR device of claim 1, wherein the second intensity level of the second scene is associated with a lower amount of intensity as compared to the first intensity level of the first scene.

4. The XR device of claim 1, wherein the first intensity level of the first scene and the second intensity level of the second scene are associated with a same amount of intensity.

5. The XR device of claim 1, wherein the first intensity level is associated with a first set of health data characteristics and the second intensity level is associated with a second set of health data characteristics.

6. The XR device of claim 1, wherein the threshold is further specific to a training objective, and the one or more components are configured to:
provide, via the interface, a notification indicating whether the second health data satisfies the threshold.

7. The XR device of claim 1, wherein:
the one or more health monitoring sensors include one or more of: a heart rate monitor, an electroencephalogram (EEG) monitor, an eye tracking camera, a pupil dilation camera, or an accelerometer; and
the second health data includes one or more of: heart rate data, EEG data, eye tracking data, pupil dilation data, or movement data.

8. The XR device of claim 1, wherein the health profile associated with the user indicates one or more of: a health condition of the user, a maximum allowed heart rate due to the health condition of the user, a maximum heart rate variability due to the health condition of the user, a target level of neural activity based on the health condition of the user, or a maximum allowed amount of movement due to the health condition of the user, and wherein the health condition is a physical health condition or a mental health condition.

9. The XR device of claim 1, wherein the one or more components are configured to:
provide, via the interface, a request for the user to perform the virtual task, wherein collecting the first health data is based on the request, and wherein generating the second scene includes performing the virtual task in the virtual environment automatically based on the second health data corresponding to the model.

10. The XR device of claim 1, wherein the one or more components are configured to:
transmit, to a server, an indication that indicates whether the second health data satisfies the threshold; and
receive, from the server, virtual environment information based on the indication, wherein the second scene is generated by the XR device based on the virtual environment information.

11. The XR device of claim 1, wherein the one or more components are configured to:
receive, from a server, virtual environment information, wherein the virtual environment information is based on information collected from a plurality of XR devices, wherein the information indicates whether health data corresponding to a plurality of users satisfies a generic threshold for scenes with certain intensity levels, and wherein the second scene is generated by the XR device based on the virtual environment information.

12. The XR device of claim 1, wherein:
the first scene in the virtual environment is associated with one or more events that cause the first intensity level; and
the second scene in the virtual environment is associated with one or more events that cause the second intensity level.

13. The XR device of claim 1, wherein the first scene and the second scene are three-dimensional scenes in the virtual environment.

14. The XR device of claim 1, wherein the second health data of the user is indicative of an emotion associated with the user and corresponding to the first scene being provided, wherein the emotion is one of happiness, sadness, fear, anger, or surprise.

15. A method, comprising:
generating, by an extended reality (XR) device, a first event in a virtual environment, wherein the first event is associated with a first difficulty level;
providing, via an interface of the XR device, the first event;
collecting, by the XR device, first vital information from a user of the XR device while the user performs a virtual task multiple times in the virtual environment, the first vital information being indicative of neural activity that is expressed in electrical signals;
forming, by the XR device, a model of the first vital information based on the electrical signals associated with the neural activity;
detecting, by the XR device, second vital information of the user, wherein the second vital information is associated with the first event, and wherein the second vital information indicates an engagement level of the user with respect to the first event;
determining, by the XR device, whether the second vital information satisfies a threshold, wherein the threshold is specific to a health profile associated with the user;
transmitting, to a server, an indication that indicates whether the second vital information satisfies the threshold;
receiving, from the server, virtual environment information, wherein the virtual environment information is based on whether the second vital information satisfies the threshold;
determining whether the second vital information corresponds to the model;
generating, by the XR device, a second event in the virtual environment based on the virtual environment information and based on whether the second vital information corresponds to the model, wherein the second event is associated with a second difficulty level; and
providing, via the interface, the second event.

16. The method of claim 15, wherein the second difficulty level of the second event is associated with a higher amount of difficulty as compared to the first difficulty level of the first event.

17. The method of claim 15, wherein the second difficulty level of the second event is associated with a lower amount of difficulty as compared to the first difficulty level of the first event.

18. The method of claim 15, wherein the virtual environment information is based on information collected from a plurality of XR devices, and wherein the information indicates whether health data corresponding to a plurality of users satisfies a generic threshold for events associated with certain difficulty levels.

19. The method of claim 15, further comprising:
providing, via the interface, a notification that indicates whether the second event is less intense or more intense than the first event based on the second vital information.

20. The method of claim 15, wherein detecting the second vital information of the user is based on one or more of: a heart rate monitor, an electroencephalogram (EEG) monitor, an eye tracking camera, a pupil dilation camera, or an accelerometer.

21. The method of claim 15, wherein the second vital information includes one or more of:
heart rate data, EEG data, eye tracking data, pupil dilation data, or movement data.

22. The method of claim 15, wherein the health profile associated with the user indicates one or more of: a health condition of the user, a maximum allowed heart rate due to the health condition of the user, a maximum heart rate variability due to the health condition of the user, a target level of neural activity based on the health condition of the user, or a maximum allowed amount of movement due to the health condition of the user, and wherein the health condition is a physical health condition or a mental health condition.

23. A system, comprising:
a plurality of extended reality (XR) devices; and
a server comprising one or more components configured to:
generate first virtual environment information for generating first content associated with first intensity levels;
transmit, to the plurality of XR devices, the first virtual environment information;
receive, from the plurality of XR devices, feedback indicating whether health data associated with the first content satisfies one or more thresholds, wherein the health data is associated with a plurality of users associated with the plurality of XR devices, respectively, and wherein the health data is indicative of neural activity expressed in electrical signals that are collected from a respective user associated with a respective XR device of the plurality of XR devices while the respective user performs a virtual task multiple times in a virtual environment;

generate, based on the feedback, second virtual environment information for generating second content associated with second intensity levels that are different from the first intensity levels; and transmit, to the plurality of XR devices, the second virtual environment information, wherein each of the plurality of XR devices comprises one or more components configured to:

form a model of the health data based on the electrical signals associated with the neural activity;

determine whether subsequent health data corresponds to the model; and generate the second content based on whether the subsequent health data corresponds to the model.

24. The system of claim 23, wherein the one or more components, of the plurality of XR devices, are further configured to:

generate the first content based on the first virtual environment information; and generate the second content based on the second virtual environment information.

25. The system of claim 23, wherein:

the health data is one or more of: heart rate data, EEG data, eye tracking data, pupil dilation data, or movement data; and the health data is indicative of emotions associated with the first content.

* * * * *